United States Patent [19]
Tamaro

[11] Patent Number: 5,810,784
[45] Date of Patent: Sep. 22, 1998

[54] SAFETY CAP ASSEMBLY FOR NEEDLES AND CATHETERS

[76] Inventor: Frank A. Tamaro, 22 Pancake Hollow Dr., Wayne, N.J. 07470

[21] Appl. No.: 912,278

[22] Filed: Aug. 15, 1997

[51] Int. Cl.[6] ..................................................... A61M 5/00
[52] U.S. Cl. .......................... 604/263; 604/192; 128/919
[58] Field of Search .................................... 604/263, 198, 604/192, 187, 110; 128/919

[56] References Cited

U.S. PATENT DOCUMENTS

| | | | |
|---|---|---|---|
| 5,261,894 | 11/1993 | Smith et al. | 604/263 X |
| 5,295,972 | 3/1994 | Mischenko | 604/192 |
| 5,531,704 | 7/1996 | Knotek | 604/263 X |
| 5,549,568 | 8/1996 | Shields | 604/192 |
| 5,591,133 | 1/1997 | Feverborn et al. | 604/263 X |

*Primary Examiner*—John D. Yasko
*Attorney, Agent, or Firm*—W. Patrick Quast, Esq.

[57] ABSTRACT

A safety needle cap assembly for needles and catheters is described. In place of the usual safety cap which requires a doctor, dentist or nurse to manually place it in position on a used syringe needle, the safety needle cap assembly of the invention automatically caps the used needle the instant the needle is withdrawn from the patient. An elastic sheath or spring attached to a safety needle cap is kept under tension, retracting the cap and allowing the needle tip to be exposed. Once used and removed from the patient, the elastic tension is released, causing the safety needle cap to snap over the used needle tip automatically, without any operator assistance. The design of the safety needle cap assembly as described includes at least needle clogging material disposed in the safety needle cap to fill the tip of the needle therewith so as to entrap the fluid contained therein. This can be combined with needle capturing material to further enhance the safety features of the assembly. A piggyback adaptation of the design permits its use in angio or intra catheter medical procedures.

9 Claims, 15 Drawing Sheets

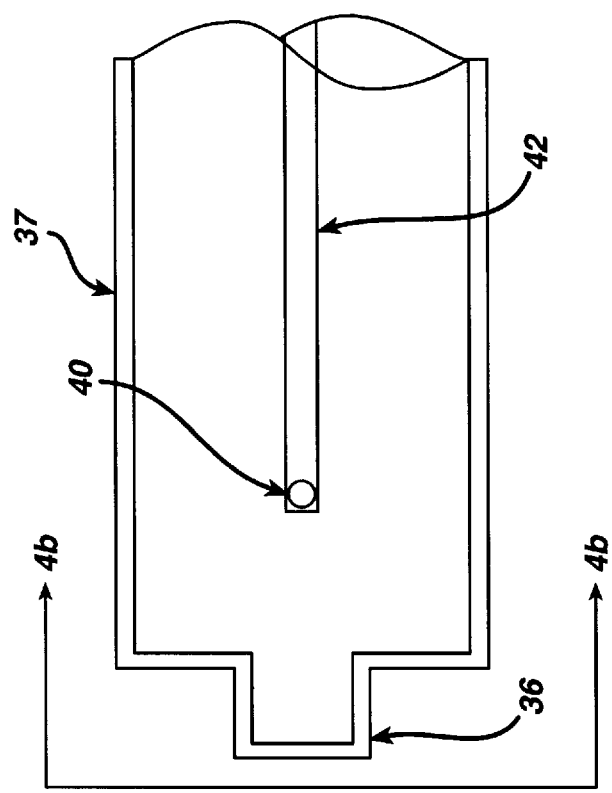
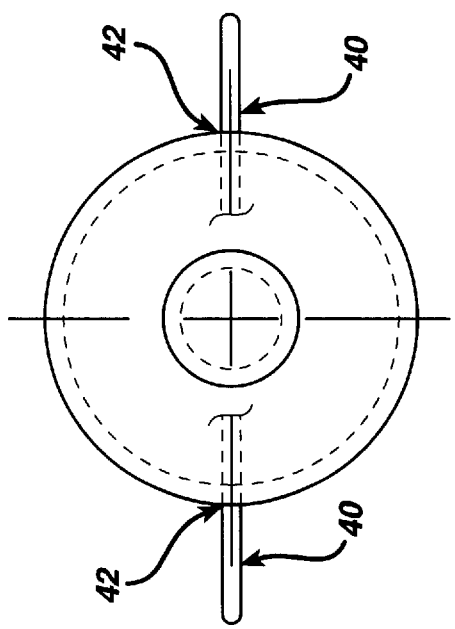

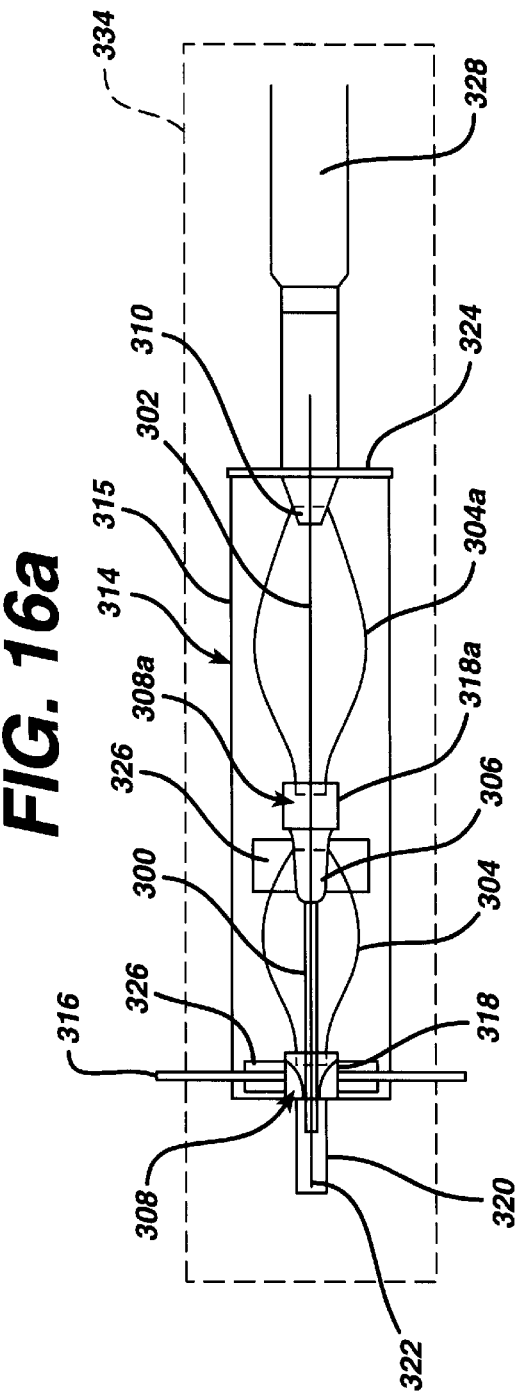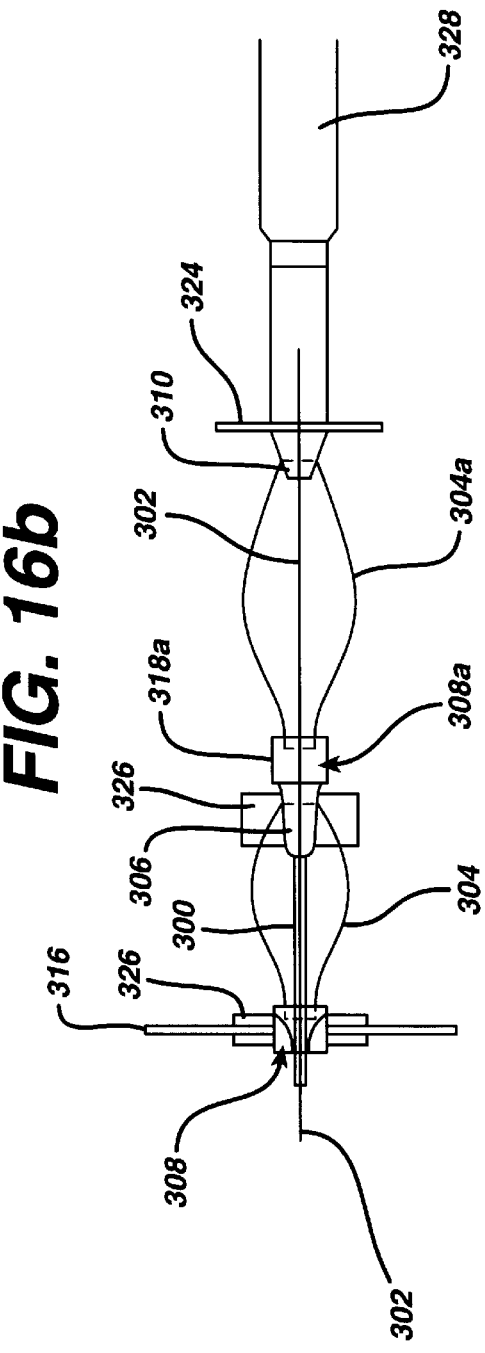

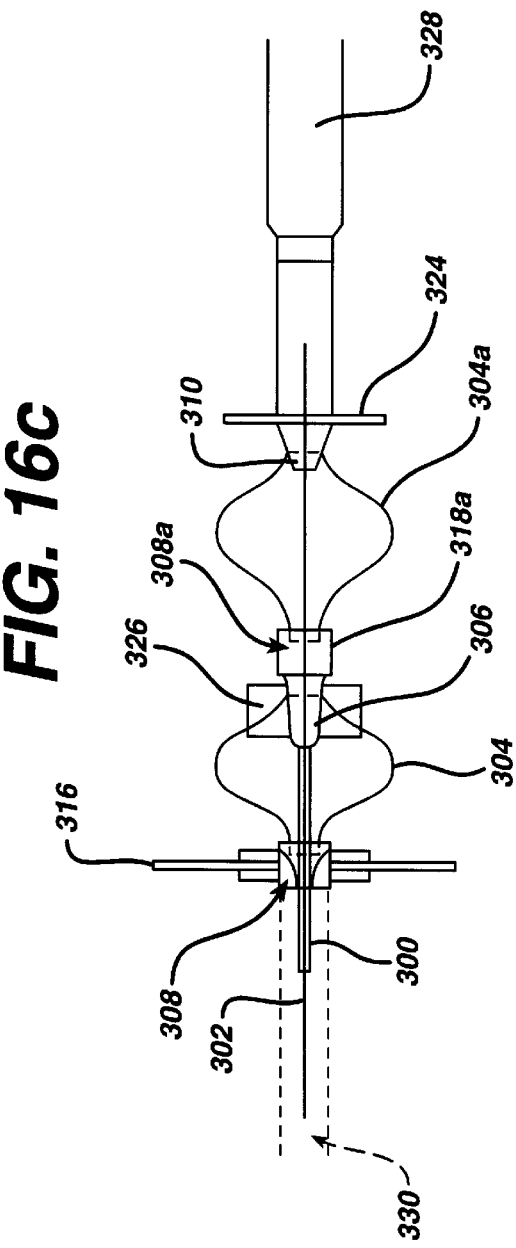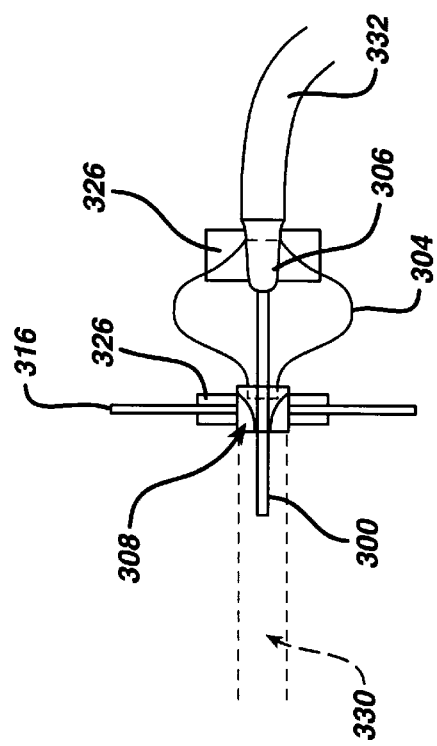

SAFETY CAP ASSEMBLY FOR NEEDLES AND CATHETERS

BACKGROUND

This invention relates to safety cap assemblies for needles, and in particular, safety cap assemblies for needles used in health-care related procedures.

Needles are, of course, employed in a wide variety of dental and medical procedures, including giving vaccines to patients, the injection of antibiotics, anesthetics, medicines, etc., the drawing of blood samples, intravenous feedings, and so on. Virtually all of these procedures subject medical personnel to the dangers of accidental sticking of the needle into a portion of their own bodies. The danger to the medical professional is primarily due to the possibility of accidentally injecting him or herself with an infectious pathogen derived from the patient after an injection has been delivered to the patient. At the present time, one need only mention the dread acronym "AIDS", (Acquired Immune Deficiency Syndrome) to understand the very real fears of the health professional.

Numerous devices have been suggested and employed to alleviate this problem. However, these devices and techniques require the knowledgeable, conscious cooperation of the physician, dentist, or nurse. Any distraction at the moment a used needle should be safety capped can result in a needle remaining uncapped, and hence a danger to anyone who might come in contact with it. This invention overcomes these disadvantages by providing a safety cap for needles that automatically safety caps the needle at the precise moment the needle is withdrawn from the patient.

The present invention is a modification of the one described in the applicant's recent patent, U.S. Pat. No. 5,630,803, which issued on May 20, 1997; and also of the inventions disclosed in three divisional cases filed by the applicant on May 19, 1997, based on the application supporting the issued patent.

The primary object of this invention is to provide a safety cap assembly for needles which automatically safety caps the needle at the moment the needle is withdrawn from the patient, thereby significantly reducing the possibility of accidental injection.

A further object of the invention is to provide for automatic safety capping of used needles without the requirement of any operator attention.

An additional object of the invention is to provide for automatic safety capping of used needles without the requirement of any operator manipulation to accomplish this safety capping.

Still another object is to provide an automatic safety cap assembly for needles which is light in weight and inexpensive to manufacture.

An additional object of the invention, is to provide an automatic safety cap assembly that cannot inadvertently expose a used needle.

Another object of the invention is to provide an automatic safety cap assembly for virtually any length and gauge of needle.

A still further object of the invention, is to provide means for sealing the needle opening so that the flow of medicine is stopped, if a needle inadvertently withdraws from the patient; or body fluids are retained, after completion of a test.

Yet another object, employing the principles of the invention, is to provide means for sealing a catheter used in angio catheter or intra catheter medical procedures.

SUMMARY

These and other objects are obtained in the instant invention of a safety needle cap for needles used in health-care related procedures.

Syringes, medicine delivery systems, etc. (hereinafter referred to as a "system") are supplied to the medical professional in a variety of ways. They may be made of glass or plastic, with attached, or to be attached needles usually being fabricated in metal, often stainless steel. A system may be supplied filled with appropriate medications, etc., or empty, depending upon the use to be employed. In any case, when a system combined with a needle is being used, the needle is connected to the base of the system by means of an enlarged structure (relative to the diameter of the needle itself) which is either a structural part of the needle, or the system to which the needle is affixed. This enlarged structure which connects the needle to the system, providing a conduit within this structure for fluid flow between the needle and the syringe, is commonly referred to as the needle "hub".

I have found that a safety cap means and an elastic sheath means combination can be fabricated so as to be put in place on virtually any needle assembly, including needle-hub assemblies and individual needles packaged in their own sterile environment. And, of course, the safety cap-elastic sheath assembly combination can be supplied already in place on systems with needles previously connected. The safety cap means of the invention consists essentially of a cap, which can be fabricated in metal or preferably economically molded in a suitable plastic such as, for example, polycarbonate, or any material, which is impenetrable for the particular gauge needle to be enclosed. The elastic sheath means attached to the safety cap means can be fabricated in a variety of resilient materials, such as for example, latex or natural rubber, plastic elastomers, or even plastic or metal springs. By the term "elastic", it is meant a material or structure which is capable of being stretched or compressed, and which, upon release of the stretching or compressing forces, returns substantially to its original shape.

These are covered in detail in the aforementioned patent and divisional applications. An overview of each follows, In a first version of the invention to be described, one end of a latex rubber sleeve is attached over the needle hub, while at the other end of the sleeve, a safety needle cap is attached. The safety needle cap can be in a variety of shapes and sizes, a tubular shape being considered practical. This tubular shaped cap is completely open at one end and is connected to the elastic latex sleeve. The other end of the cap is closed except for an opening just large enough to accommodate passage of the particular gauge needle being used. The safety needle cap is attached to the sleeve so that the needle opening at the end of the cap is sufficiently misaligned from axial alignment with the needle, when the latex sleeve is not being compressed, so as to preclude accidental, re entry of the needle through the hole.

In this embodiment, to use the system, the operator would manually position the safety cap so that its opening is in axial alignment with the needle. He would then push the needle through the opening in the cap- the elastic, latex sleeve now being compressed and put under tension by this action of the operator. Depending on the inherent resilience of the elastomeric material employed, axially extending slits, if necessary, running partially along the length of the latex sheath, can facilitate this compression of the sheath. With the needle now exposed, the health professional can now proceed and insert the needle into the patient. The safety needle cap now is in contact with the patient, as for example, the arm of the patient, the cap simply riding back over the needle as the sheath is further contracted by the force applied by the health professional in inserting the needle to the required depth. After the injection, the operator simply withdraws the needle from the patient without the necessity of any thought being given to the safety needle cap. The instant the needle is free of the patient, the elastic tension in the compressed latex sheath is released, causing the safety cap to snap back to its original, off-axis or quiescent position. The needle tip is now safely contained within the needle cap where, of course, it cannot, inadvertently reenter the cap opening. The enclosed needle-hub combination can now be safely disposed of by a health professional, or technician, without any danger of accidentally causing the tip of the needle to protrude form the cap. The entire capping procedure is accomplished automatically, and without reference to the alertness or lack thereof of the operator.

Additional conveniences can be added to the above described device and procedure. For example, in a second version to be described, the safety needle cap-elastic sheath assembly can be supplied with a safety needle assembly enclosure having slots along its length to accommodate oppositely positioned projecting arms fixed to the safety needle cap. In this version, the cap and sheath means and needle would be supplied enclosed within this needle assembly enclosure. This is done with or without the assembly already in place on a system. The projecting arms on the safety needle cap project through the slots within the safety needle assembly enclosure. The needle is in axial alignment with the needle opening within the cap, with the tip of the needle now protruding through this needle opening. In this manner, the device is supplied in a ready-to-operate configuration. To use this version of the invention, the operator places his or her fingers on the projecting arms of the safety needle cap, removes the safety needle assembly enclosure, and proceeds as described in the first version of the invention with the injection. Again, after the needle is removed from the patient, the safety needle cap automatically snaps back to an off-axis position where the cap opening is out of axial alignment position with the needle, so that it is safely captured within the cap.

Two basic designs for the safety cap are disclosed. The first is relatively simple and includes a front face portion including an axially disposed, needle hole of sufficient size so as to accommodate the needle gauge employed. As described, the tubular cap includes cylindrical sidewall means that connects to the elastic sheath means. The sidewall means as assembled to the elastic sheath means extends backwards, in the direction of the needle hub, a sufficient distance so that the needle tip is captured within the volume defined by said front face portion and the distal end of the sidewall when the system is in a released condition.

A second cap design includes a front face portion wherein the needle opening comprises a frusto-conically shaped opening, including a smaller opening on the interior surface of said front face portion and a larger opening on the exterior surface of said face portion. A second, rearwardly disposed face portion includes a second opening and a tubular extension extending rearwardly therefrom, the axis of the second opening and tubular extension being offset from the axis of the openings in the front portion. This axis offset feature leverages the safety cap, in relation to the needle, so that when the elastic sheath means is in its released, quiescent disposition, the axis of the needle is offset from the axis of the opening in the front face portion of the cap.

The frusto-conical opening in the front face portion is adaptable to be able to retain gauze or similar material to capture and absorb body fluids as the needle, after use, is enveloped within the cap volume defined by the front face portion and sidewalls.

Additional safety enhancing features for use with the cap of either design are disclosed. These include a flap member, hingedly connected to the cap sidewall and disposed in relation to the needle to close off the opening in the front face portion after the device is released from the compressed, sheath means, position. Alternately, the area in the vicinity of the juncture of the sidewall and face portion can be packed with the Styrofoam or similar material which will capture the needle tip in the sheath means-released position.

In a third version of the invention to be described, the elastic sheath means can be in the form of a metal or plastic spring. The purpose of this spring type of elastic sheath means is the same as for the previous two versions, i.e., to maintain the safety cap in a position so that it will automatically snap back over the needle, with the needle opening within the cap out of alignment with the axial alignment of the needle, after the needle has been withdrawn from the patient. The spring can be enclosed in its own fabric sheath so as to facilitate its connection to the safety cap and needle hub.

A further embodiment depicts the safety cap configured in an "elbow" form. In this version the axial misalignment as is necessary between the cap and the needle in the relaxed, quiescent state is inherent in the cap design.

The modification to these embodiments proposed in this invention provides for the use of needle—clogging material alone or in combination with a needle capturing material such as Styrofoam disposed in the safety needle cap.. A sealing membrane such as foil or cellophane is placed over the putty or gel-like material to minimize the drying out of the material or the risk of contact with the outer surface of the needle before use. Application of these clogging techniques to an angio or intra catheter needle sheath assembly is also disclosed.

As will be more fully discussed, the structure of the safety needle cap assembly of the invention can have further modifications to virtually rule out any possibility of inadvertently repositioning the safety needle cap after use in a way that would permit the tip of the needle to re-emerge from the needle opening within the cap. Obviously, on all versions cited above, a sterile safety package, such as a safety foil, can be provided to enclose any described safety cap means and elastic sheath means assembly as supplied with or without needles, syringes and catheters.

BRIEF DESCRIPTION OF THE DRAWINGS

FIG. 4A is a top plan view of the safety needle cap assembly enclosure and syringe depicted in FIG. 4.

FIG. 4B is a view of the cap assembly of FIG. 4A, taken along lines 4B—4B in that view.

DETAILED DESCRIPTION

As noted above, the present invention has broad application. For purposes of illustration only, the needle system to be described hereinafter will focus on the syringe system which includes a syringe barrel and plunger. The needle-hub in this system can be formed as part of the barrel or be separate therefrom and which, together with the needle, inserted typically into an opening in the syringe barrel.

Figure 1:
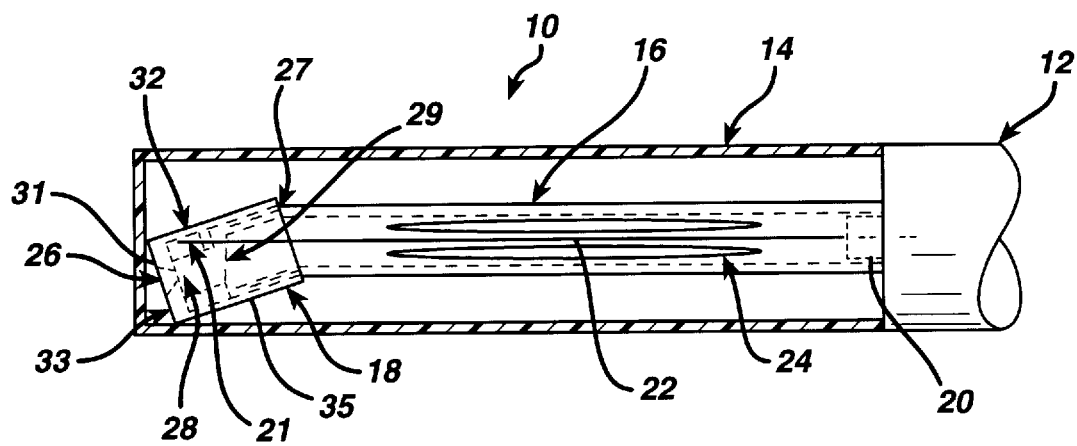
FIG. 1 is an elevational, sectional view of one version of the safety needle cap assembly of the invention.

Turning now to the drawings wherein similar structures, having identical functions, are denoted with the same numerals, FIG. 1 illustrates a complete first version 10 of the safety needle cap assembly of the invention. A syringe 12 is shown with an attached needle 22. The needle 22 is shown enclosed within an elastic sheath means 16, the elastic sheath means being connected at one end to the hub 20 of the needle, and at its other end to a safety needle cap 18. The elastic sheath means can be affixed to the needle hub and safety cap by any convenient means, such as with suitable adhesives, clips (not shown), etc. Where the elastic sheath is formed of an elastomeric material such as latex, the connection can be made by any suitable means including a frictional fit between the two pieces. The elastic sheath means 16 can be fabricated in a variety of suitable elastomers, e.g. latex rubbers, capable of being easily compressed under tension, and including a good "memory" so as to enable the elastic sheath means to return to its original shape when the tension is released. Other resilient means, for example, a spring, can be employed as the elastic sheath means as will be more fully described and illustrated in FIGS. 6, 6A and 7.

The safety needle cap 18 itself can be fabricated out of a number of hard materials, which will be impenetrable to the needle tip, for example, a clear plastic such as polycarbonate. The shape and size of the safety needle cap can vary depending on applications and design preferences, a tubular shape being suitable for some applications as depicted in FIG. 1. See also FIG. 15 and the attending description.

The tubular shaped safety needle cap is shown fully open at one end 27 for attachment to the elastic sheath 16. As is the case with the needle hub, the other end of the elastic sheath 29 can be attached to the safety needle cap by any convenient means, such as with a suitable adhesive, clips (not shown), frictional fit, etc. The other end of the safety needle cap is closed except for an interior opening 28 within the cap of just sufficient diameter as to permit the passage of the syringe needle 22 through this opening. As will be more fully illustrated and explained, this is an important feature of the invention. It virtually precludes the possibility of inadvertent, re-emergence of the tip 21 of the needle after the needle 22 has been used.

The exterior portion 26 of the interior cap opening 28 is an enlarged frusto-conical shape. It precludes body fluids on the needle from contacting the surface 31 of face portion 33. Gauze or other absorbent mesh work, (see FIGS. 14(a) and FIG. 14(b)), can be secured within the frusto-conically shaped opening to absorb any remaining body fluids on the exterior of the needle as the needle withdraws within the cap after use.

The safety needle cap 18 is affixed to the end of the elastic sheath means. The length of the sheath means between its points of attachment to the cap 18 and the hub 20 is such that the needle tip is enclosed in the volume defined by the face/portion of the cap 33 and the sidewall 35 when the sheath is in its released condition, i.e. not under compressive forces. In this relaxed state, the needle opening 28 within the cap is offset from the axial alignment of the syringe 12 and attached syringe needle 22. This arrangement positions the tip 21 of the needle along the upper wall 32 of the tubular side wall of the cap. The elastic sheath means is shown as a tube of latex rubber having slits 24, if necessary, along a portion of the length of the elastic sheath so as to facilitate compressing the sheath when required. The slits can also facilitate a "drooping" of the cap end of the sheath when the system is in the released condition. Where elastomeric material is used, the requirement for slits will depend in part on the gauge, thickness, density, etc. of the material. The entire safety needle cap 18, elastic sheath 16 and syringe needle 22, are shown enclosed in a sterile enclosure 14, which is removed at an appropriate time before use.

Figure 2:
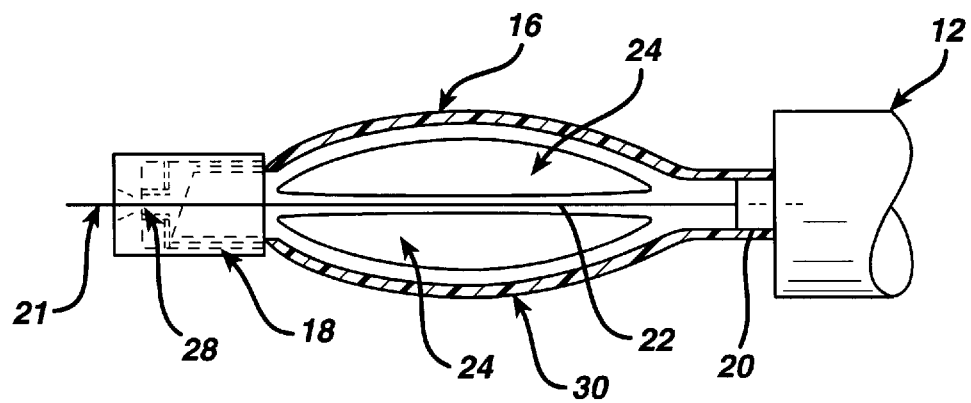
FIG. 2 is an elevational, partial sectional view of the version of the safety needle cap assembly of FIG. 1, illustrating the device ready for use.

FIG. 2 illustrates the version of the invention depicted in FIG. 1, now ready to be utilized with a patient. The sterile metal foil 14 has been removed, and the safety needle cap 18 has been manually moved (not shown) so that the needle opening 28 in the cap is in axial alignment with the hypodermic needle 22, the cap being moved longitudinally along the axis in alignment with the needle, causing the elastic sheath 16 to be compressed 30 and therefore under tension, while at the same time exposing the tip 21 of the needle 22. With the hypodermic needle 22 in this position, the needle can now be inserted into the patient to perform the required medical procedure.

Figure 3:
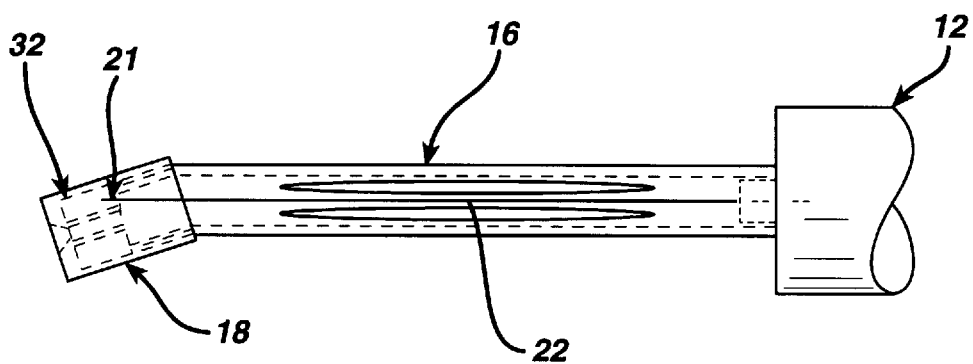
FIG. 3 is an elevational view of the device shown in FIGS. 1 and 2, illustrating the position of the safety needle cap after use.

FIG. 3 illustrates the version of the invention depicted in FIGS. 1 and 2 after the needle has been withdrawn from the patient. This procedure is best understood from FIGS. 8 and 9. The moment the needle is withdrawn from the patient, the elastic tension within the elastic sheath 16 is released which causes the safety needle cap 18 to snap back into its original position. In returning to its original position, the hypodermic needle is caused to be withdrawn to a position within the cap, with the tip 21 of the needle now harmlessly in contact with the inner surface of the upper wall 32 of the safety needle cap 18. The syringe 12 and needle 22 combination, including the safety needle cap 18 and elastic sheath 16, can now be disposed of safely. It is to be noted that the securing of the now potentially dangerous hypodermic needle within the safety needle cap of the invention is accomplished without any manual manipulations by the health professional, or even active consciousness of performing this often extremely important safety procedure.

Figure 3A:
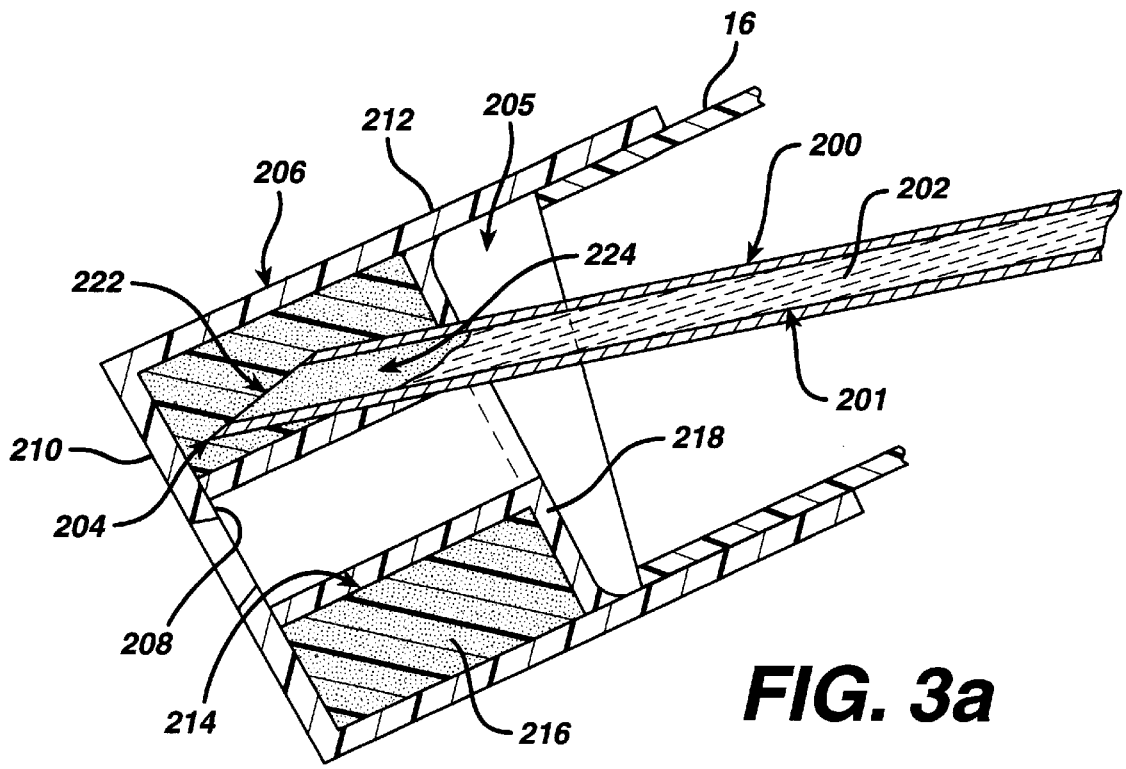
FIG. 3a is an elevational, partial sectional view showing the needle—clogging aspect of the present invention.
Figure 3B:
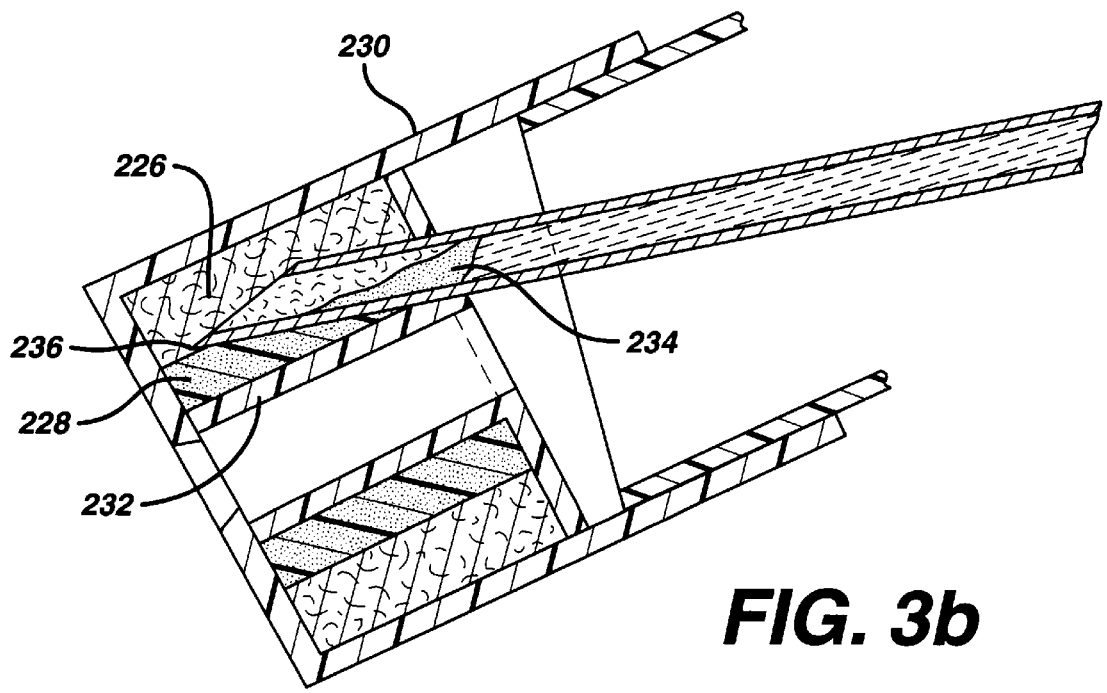
FIG. 3b is an elevational, partial sectional view showing the needle—clogging, needle—capturing feature of the present invention.

FIGS. 3a and 3b depict the particulars of the needle clogging provisions of the present invention. In FIG. 3a, the needle 200 is shown in the released condition. It has either withdrawn inadvertently, by itself, from the patient's body or the operator has intentionally done so. The needle cavity 201 is seen to still retain the fluid 202 which may be an intravenous solution or body fluid. The needle tip 204 has entered the volume 205 within the safety needle cap 206 defined by the inside surface 208 of the front face portion 210 and the sidewall 212.

Disposed in this volume in, for example, annular ring form 214 is a needle—clogging material 216 of putty, or gel-like consistency, but able to retain its shape. A suitable material, familiar to Dentists, but one of many, is CAVIT G, manufactured by EPSE company of Germany, and marketed in the U.S. through Henry Schein Incorporated, of Port Washington, N.Y. Initially of putty—like consistency, when it is contacted by fluid it hardens. The outer diameter of the ring conforms to the inner diameter of the safety cap and generally obviates the need to secure the ring to the inner surface of the cap sidewall.

Disposed over the annular ring 216 is a vapor barrier 218 which reduces the exposure of the putty or gel-like material to the air so as to keep it from drying out. The barrier also precludes contamination of the needle by material before use. Cellophane or foil is a suitable cover material.

Upon reaching the released condition, the needle tip 204, upon entering the volume 205 penetrates the barrier 218 and the ring of needle—clogging material 216. A portion of this ring enters the channel 201 containing the fluid and seals off the end 222, with the entrapped material.

As described, the improved safety needle cap eliminates the flow of fluid 202 out of the needle once the safety cap assembly has reached the released state. If the safety cap assembly forms a part of an intravenous feeding setup, where necessary fluids and/or medicants are being given to a patient, the interruption of the fluid flow caused by an inadvertent withdrawal can be made to trigger an appropriate alarm system. If body fluids are being withdrawn by an operator, the improved system will preclude accidental spillage thereof which might otherwise cause grave concern.

In FIG. 3b, a further annular ring, of needle tip—capturing material such as Styrofoam 226, is positioned between the ring of needle—clogging material 228 and the inside surface of the sidewall 230. A vapor barrier 232 is also utilized. In this further adaptation, after the needle has become clogged with material 234, the needle tip 236 embeds itself in the Styrofoam ring 226 further enhancing the safety features of the system by reducing significantly or eliminating completely the possibility that the needle will prick someone's body.

Figure 4:
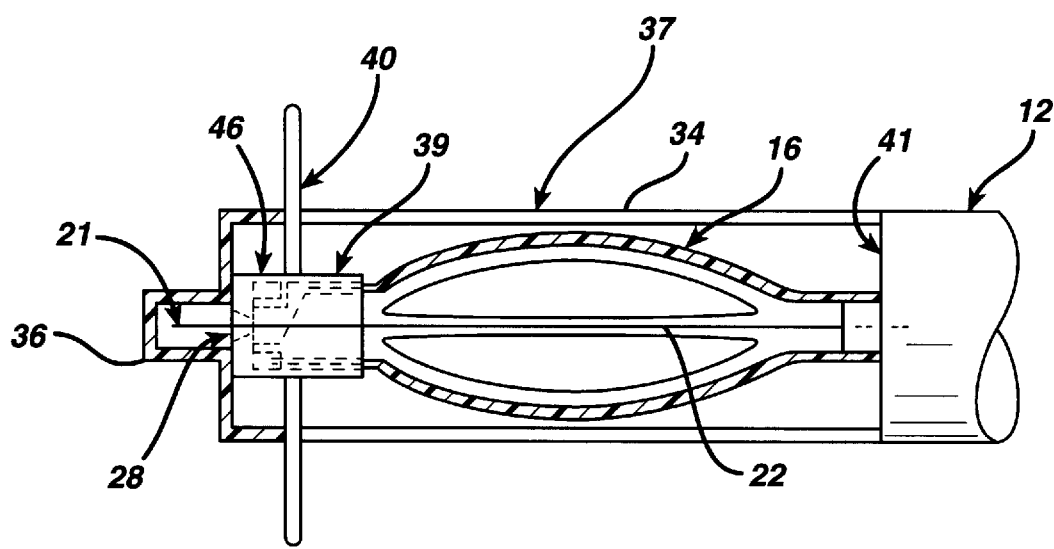
FIG. 4 is an elevational, partial sectional view of a version of the invention, showing a safety needle cap assembly enclosure and modified safety needle cap positioning the needle in ready for use, axial alignment with the needle opening within the cap.

FIG. 4 illustrates a second version of the invention in which a safety needle enclosure assembly 37 cooperates with a modified safety needle cap 39. The modified safety needle cap 39 includes arms 40 attached to and projecting radially outward from the side wall 46 of the modified cap. Other alternate configurations and attachments for the arms are disclosed in one of my copending applications. The attached arms 40 project through slots 42 in the safety needle enclosure assembly 37 (FIG. 4A). The axial length of the enclosure assembly 37 and length of slots 42 are such, that, when the assembly 37 and sheath-cap combination 16–39 are in place on the syringe-needle combination, with the one end of the sheath means secured to the needle hub 20, the arms 40 cooperate with the closed ends of slots 42 to maintain the elastic sheath in a contracted, compressed condition under elastic tension. The safety needle enclosure assembly 37 itself can be fabricated in a variety of plastic materials. The safety needle enclosure assembly 37 can have a smaller diameter tubular extension 36 sealed at one end, forming a safety cover for the now exposed tip 21 of the needle. The smaller diameter tubular extension 36 is confluent with a larger diameter tubular extension 34. The open end of the latter contacts the syringe barrel at surface 41 when the assembly-cap-sheath combination, 37–39-16, are arranged in place.

The enclosure 37 including its length and the relative diameter of tubular extension 36, can be designed so that the outside surface of the face portion of cap 39 (corresponding to surface 31—see FIG. 1) contacts the interior surface of the vertical section (as seen in FIG. 4) disposed between the tubular extensions 34 and 36 and before arms 40 ever reach the closed ends of the slots. This design, alternately, can maintain the safety needle cap assembly in a ready condition.

To use the device illustrated in FIGS. 4 and 4A, once the sheath is connected to the hub 20, the operator would grasp the arms 40 extending through the slots 42 in the safety needle enclosure assembly with his or her fingers. The operator would then pull the safety needle enclosure 37 off from its contact with the syringe barrel with his or her free hand. With the tip 21 of the needle 22 now exposed and properly aligned, the operator can now proceed with the medical procedure.

Figure 5:
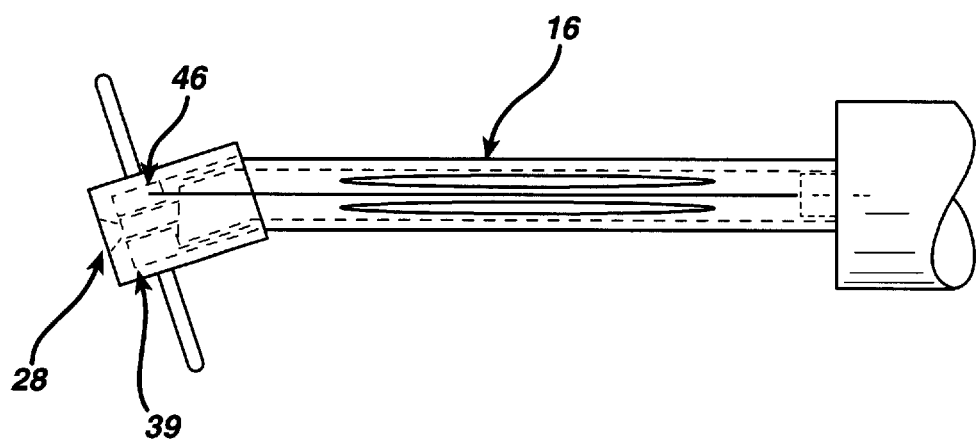
FIG. 5 is an elevational view of the invention depicted in FIG. 4, illustrating the position of the safety needle cap after use.

As shown in FIG. 5, after the needle is withdrawn from the patient, the elastic tension is released in the elastic sheath 16, which causes the modified safety needle cap 39 to move forward to a position where it encloses the needle tip, the tip of the needle now embedding in needle clogging material, and needle capturing material.

Figure 6A:
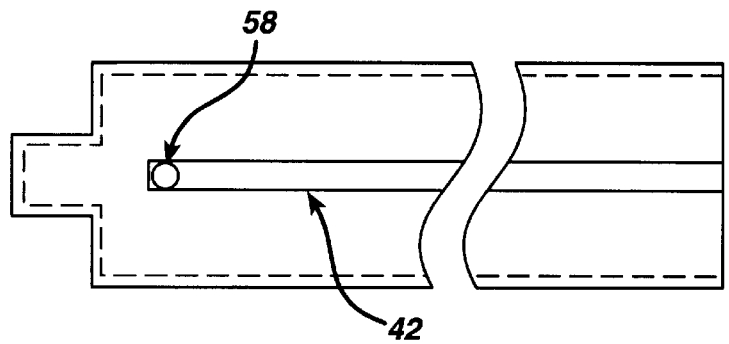
FIG. 6A is a top plan view of a part of the safety needle cap assembly enclosure and syringe depicted in FIG. 6.
Figure 6:
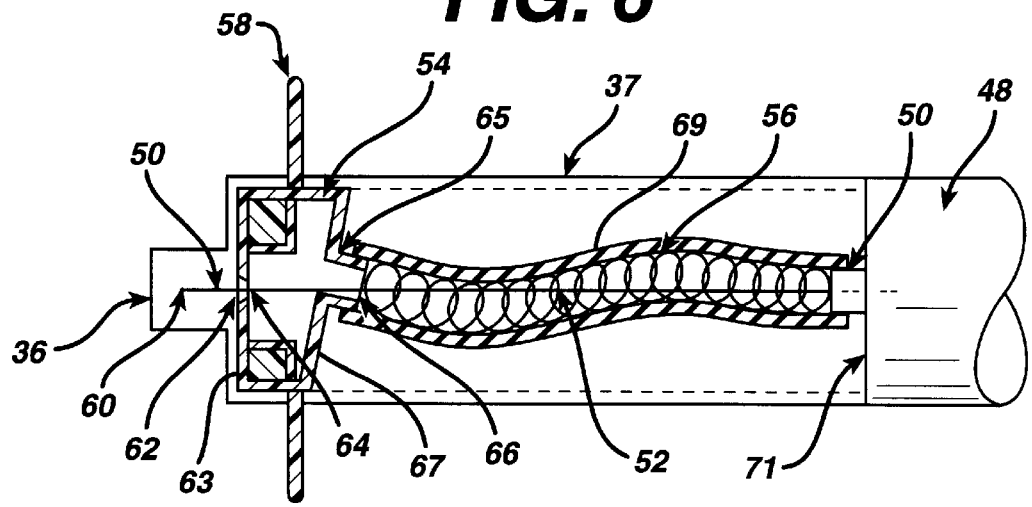
FIG. 6 is an elevational, partial sectional view of a version of the invention which employs a spring for the elastic sheath means, and depicts a second embodiment of the safety needle cap means.
Figure 7:
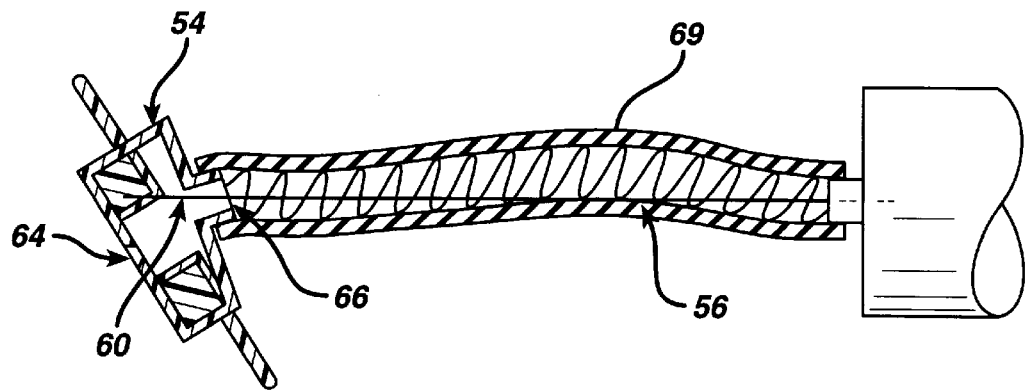
FIG. 7 is an elevational view of the invention depicted in FIG. 6, showing the position of the safety needle cap after use and depicting the interface between the needle and clogging material.

In FIGS. 6, 6A and 7, a further version of the invention is illustrated depicting the use of a spring 56 as the elastic sheath means, and illustrating a further modified safety needle cap 54. As described above for FIGS. 4 and 4A a safety needle enclosure assembly 37 encloses the further modified cap 54 and spring elastic sheath 56. The spring elastic sheath 56 is placed in compression as described above. Needle 50 is aligned with rear opening 66. The needle is axially aligned with a smaller internal needle opening 64 and a larger, exterior frusto-conical needle opening 62 in a front face portion 63 of cap 54 so that the needle extends through the cap with the tip of the needle 60 now exposed beyond the cap 54, but protected by the tubular extension 36 of the safety needle enclosure assembly 37. The principal modification shown to the cap 54 is that, instead of having a fully opened rear portion of the cap as described in FIGS. 1–5, the rear portion of the cap is substantially closed, by a back face portion 67 which includes a tubular extension 65 having an opening 66. One end of the spring 56 is attached to this tapered tube 65 again in any convenient manner, such as adhesively or with a clamp (not shown), with the other end of the spring 56 similarly attached to needle-hub 50. The spring can be enclosed in a sleeve 69 made of compliant material such as nylon or the like, or even an elastomeric material, such as latex. One end of the fabric enclosure is attached to the extension 65 and the other end to needle hub 50. The spring 56 itself can be fabricated in a variety of suitable materials, including metal or plastic.

As can best be seen in FIG. 6, with the arms 58 secured in the slots 42 within the safety needle enclosure assembly 37, and the one end of the assembly 37 in contact with the surface 71 of the syringe 48, the spring 56 is put under elastic tension. The needle 52 enters the cap through the opening 66 in the tubular extension 65 of the cap 54 and is axially aligned with the internal needle opening 64 and external needle cap opening 62, with the tip 60 of the needle now protruding into the smaller diameter portion 36 of the safety needle enclosure assembly 37. Operator manipulations of the arms 58 and removal of the safety needle enclosure assembly 37 now permits direct utilization of the syringe 48 in the delivery of a medical procedure to a patient.

As illustrated in FIG. 7, after the needle is withdrawn from the patient, the spring tension is released, and the tip 60 of the needle now automatically is positioned within the further modified safety needle cap 54 embedded in needle clogging material. The opening 64 in the front of the cap and the opening 66 at the rear of the cap are now misaligned to a degree that virtually precludes any possibility of accidentally realigning the needle with the opening 64.

Figure 8:
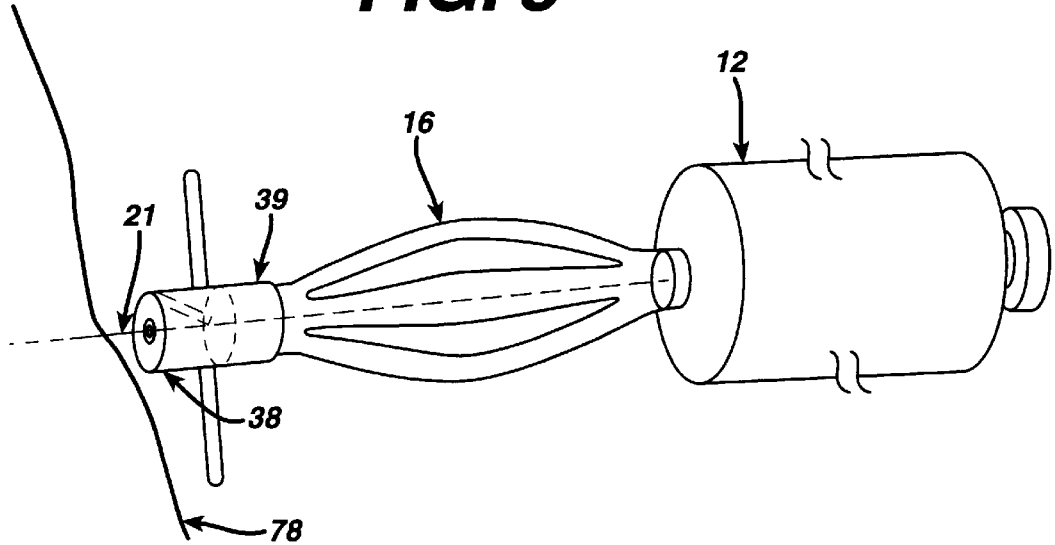
FIG. 8 is a perspective view of one version of the invention as being used to deliver an injection to the arm of a patient.
Figure 9:
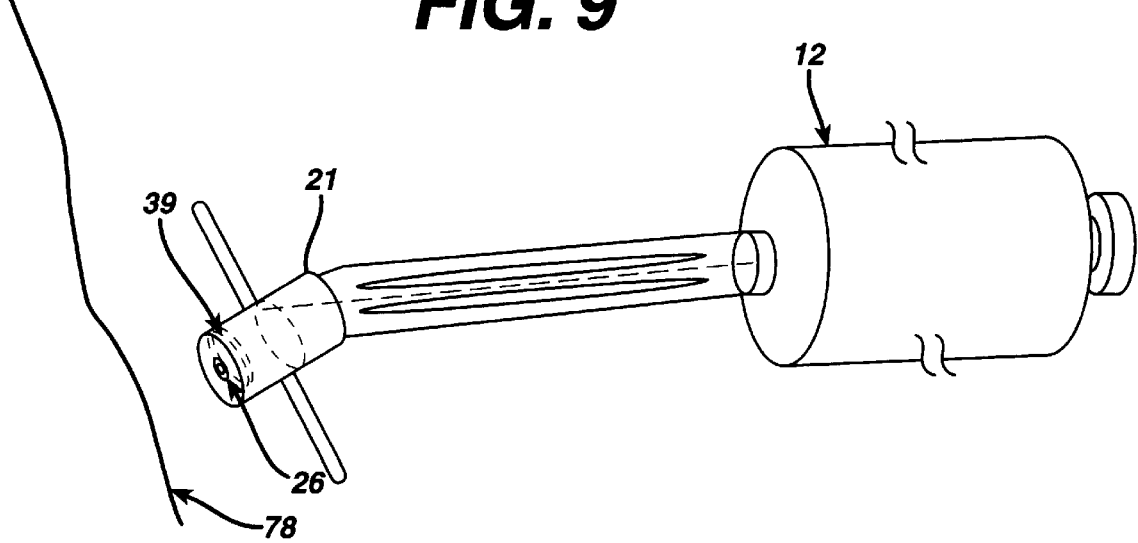
FIG. 9 illustrates the version of the invention as depicted in FIG. 8 after the needle has been withdrawn from the patient's arm.

FIGS. 8 and 9 illustrate the second version of the invention depicted in FIGS. 4, 4A and 5 in actual use on a patient. The tip 21 of the needle is shown penetrating the skin on the arm 78 of a patient with the lower bottom edge 38 of the tubular shaped modified safety needle cap 39 in contact with the skin. This serves to aid in maintaining the cap in a withdrawn position, thus sustaining the tension in the elastic sheath means 16 while a medical procedure is in progress.. Once the procedure is completed and the needle withdrawn, FIG. 9, the safety needle cap of the invention snaps over the tip of the needle, safely enclosing the potentially dangerous needle. Although not depicted, needle clogging material can be utilized to close off the needle opening.

Figure 10:
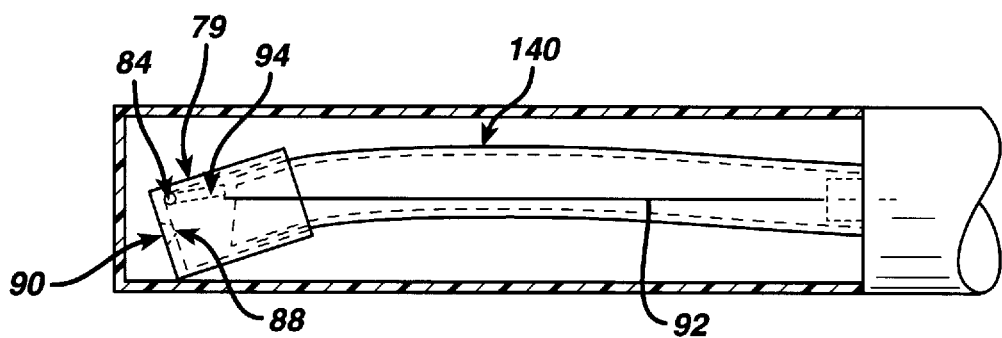
FIGS. 10, 11(a), 11(b), 12(a), 12(b) depict in elevational views a modification to the safety cap feature of the invention.
Figure 11B:
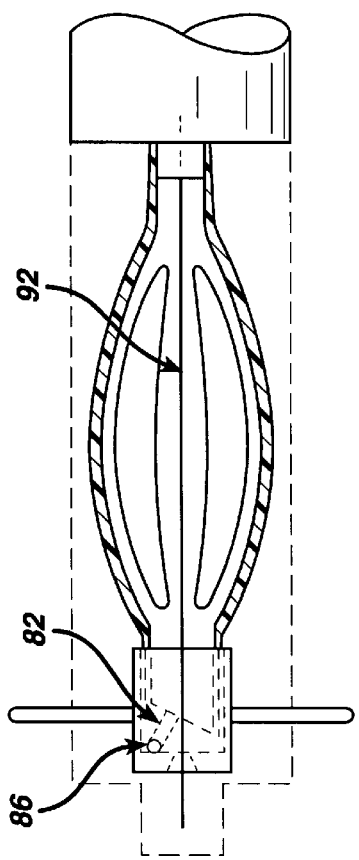
Figure 11A:
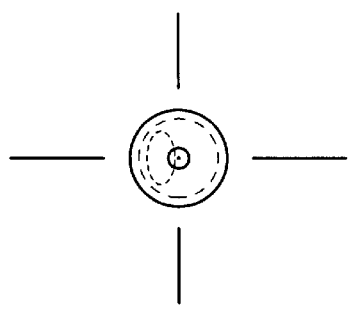
Figure 12B:
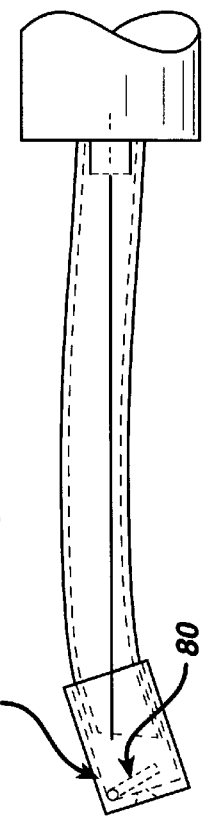
Figure 12A:
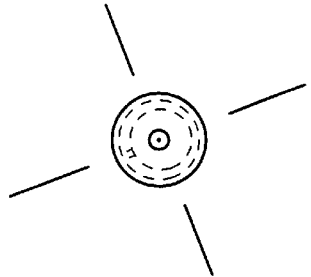

FIGS. 10 through 12 depict supplementary adaptations of the cap member which, if necessary, could be used to ensure the capture of the needle tip after use. FIGS. 10, 11(a), (b) and 12(a) (b) illustrate a modified version of the safety cap 79. This modification depicts the incorporation of a closure means 80 including a flap member 82 hinged at 84 to the sidewall 86. The flap member is of sufficient size and hinged to the sidewall in a manner that it closes off the interior side 88 of the opening 90 when the cap-sheath assembly is in its extended position as shown in FIG. 12(a) and 12(b). FIG. 10 shows the relationship of the flap member 82 to the needle 92 when the cap-sheath assembly is first connected to the needle-syringe assembly. The needle contacts surface 94 of the flap member and captures the flap member 82 between itself and the sidewall 96. This permits the subsequent operation of aligning the needle 92 with the opening 90 in readying the syringe-sheath assembly for use.

FIG. 11(a) and 11(b) indicate the relationship when the needle is axially aligned and positioned through the opening 90. In this view, the flap member 82 rests on the surface of the needle 92.

The hinged flap member can be included as part of the plastic mold used in forming the cap so that the formed cap product would include the flap member as an integral part. The flap member can be employed with any of the cap members, 18, 39 and 54 described above or as described below in FIG. 15.

Although not depicted, needle clogging material can be utilized to close off the needle opening.

Figure 13:
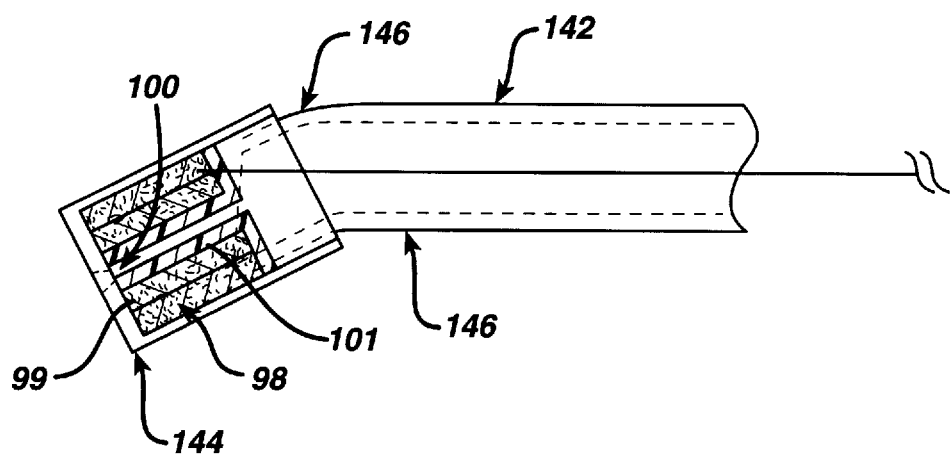
FIG. 13 depicts yet another modification of the safety cap including the needle clogging and capturing features of the invention; and, an adaptation of the elastic sheath means portion.

FIG. 13 illustrates the use of an annular ring of Styrofoam or similar material 98 to capture and retain the needle point after the medical procedure. The ring is placed inside the cap and secured with appropriate means such as adhesive, at the juncture between the sidewall and interior surface of the face portion. The annular ring as positioned and constructed of course, would permit needle access to opening 100 during set up. Further, a ring of needle clogging material, 99, is disposed between the opening 100 in the front face portion and the ring of Styrofoam 98. A vapor barrier 101 acts to prevent the material from drying out.

Figure 14A:
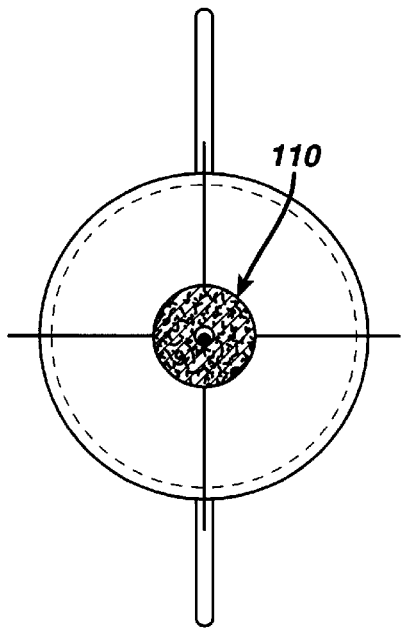
FIGS. 14(a) and 14(b) depict in front elevational and side, sectional elevational views the details of one embodiment of the safety cap including the needle clogging feature of the invention.
Figure 14B:
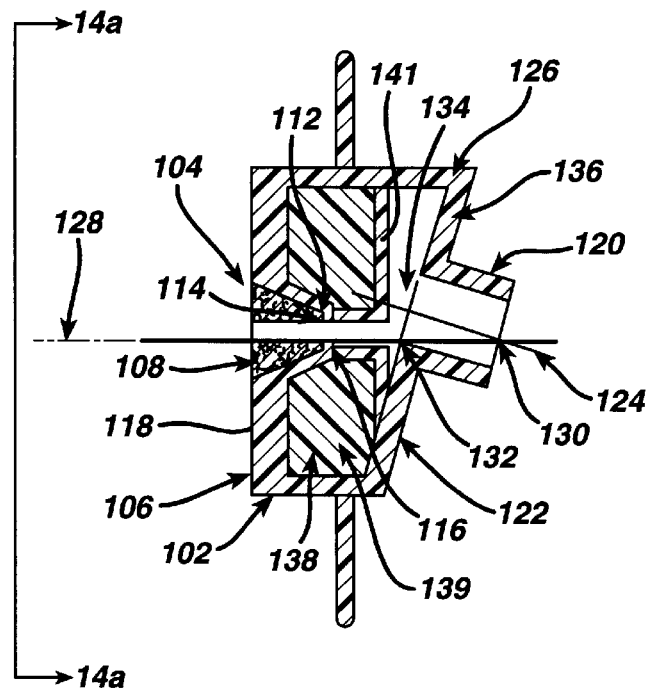

FIGS. 14(a) and 14(b) disclose in close-up a cap member 102 which depicts the preferred construction of the frusto-conical opening 104 in the front face portion 106 and how gauze 108 or other similarly, absorbent material is disposed therein. The gauze is positioned in the frusto-conical opening and secured by a suitable adhesive. Although the cap style depicted is similar to cap 54 above, the configuration of the opening 104 is also appropriate, of course, for the front face portion of any cap configuration including 18 and 39 described earlier or as described below for the cap design of FIG. 15.

The opening 104 includes a first, larger opening 110, which tapers back to a second opening 112, which may be further reduced in size to a third opening 114 by an annular shelf portion 116. The shelf portion can be included in the cap design, if necessary, to facilitate the placement and retention of the gauze 108. Of course, third opening 114 is of sufficient diameter to permit passage therethrough of the particular needle to be used. Preferably the diameter of the first opening 110 is sufficiently large, so that droplets of body fluid which may adhere to the needle as it is withdrawn from the patient do not bridge the space between the needle and the outer surface 118 of the face portion 106.

FIG. 14(b) is also helpful in illustrating an important feature of the style cap depicted (and style 54 of FIG. 6). Tubular extension 120 formed in back face portion 122, is centered on axis 124 which is offset in relation to the axis of the frusto-conical opening 104 on the front face portion. Both before readying the cap-sheath assembly and the needle-syringe assembly prior to use, and after withdrawing the needle from the patient when the sheath means relaxes and the needle tip is captured within the volume defined by the front face portion 106, back face portion 122 and the sidewall 126, the tubular extension 120 serves a useful purpose. The tubular extension 120 and more particularly the angular orientation of back face portion 122 in relation to the front face portion, ensures that the needle is orientated in a direction essentially parallel to axis 124, and necessarily, is offset to the axis 128 that the needle aligns itself to when it is inserted through the opening 114. In effect, the cap 102 pivots about the needle 130 at point 132 of the opening 134 on the interior surface 136 of the back face portion 122 whenever the needle tip is positioned in the interior volume 138 as defined by the face portions and sidewall. This occurs, again, prior to readying the assembled cap-sheath-needle-syringe assembly and after the relaxed sheath means moves the cap forward, after use, and the needle enters the volume 138, offset from axis 128. This precludes reentry through opening 114.

Further a ring of needle-clogging material 139 and vapor barrier 141 are employed to prevent loss of fluid from the captured needle.

Finally, referring for the moment to FIGS. 10 and 12(b) assume the sheath means therein depicted, 140, is fabricated from an elastomeric material such as latex. For the particular cap design illustrated and cap design 18 and 39 above, i.e. designs without the back face portion such as 122 in FIG. 14(b), it is of benefit, depending on its thickness and material, that the elastomeric sleeve tends to arc, as depicted, due to the weight of the cap when the needle withdraws into the interior volume of the cap. Thus in this relaxed state the effect of gravity can cause the cap end of the sheath to droop or arc so that the needle opening 100 within the cap is offset from axial alignment with the needle 92. Alternately, the elastomeric sleeve can be formed at manufacture to include the arc. This inherently results in the opening in the cap, 90, being offset to the axis of the needle, thus advancing the purposes of the invention.

FIG. 13 depicts an alternate sheath means 142. The sheath means in this embodiment is fabricated with a suitable bend 146 formed in the material to ensure that opening 100 will be offset from the needle axis when the needle tip is positioned within the cap volume.

Figure 15:
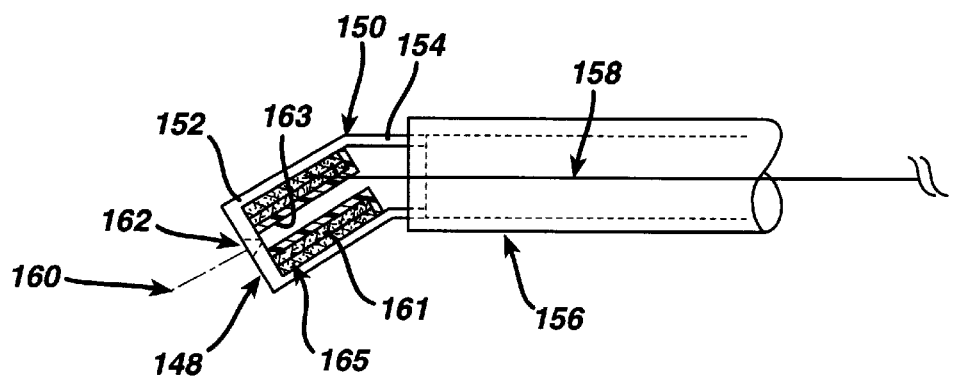
FIG. 15 is a partial, elevational view depicting a further embodiment of the safety cap which is formed in an elbow configuration to accommodate the purposes of the invention including the needle clogging and capturing features.

In order to provide the offset from the needle axis as required, yet another embodiment as seen in FIG. 15 depicts the cap 148 as fabricated with an angular offset 150 between a front portion 152 and rear portion 154. Here, of necessity, irrespective of the orientation assumed by the sheath means 156 in the relaxed condition, the needle 158 is offset from the axis 160 of the opening 162. The needle is thus precluded from re entering the opening unintendedly. Needle clogging material 161, suitable barrier material 163 and needle capturing material 165 are utilized for the purposes of the invention.

While the description has centered around clogging and embedding the tip of a needle, the present invention also has application to angio or intra catheter medical procedures. Here a sheath—like member is initially in position over the tip end of a needle. The needle is inserted into the patient and the sheath—like member penetrates the flesh and becomes lodged in the skin. The sheath—like member functions like the needle tip, making it a candidate for the needle clogging and needle entrapping features of the present invention.

FIGS. 16a through 16e illustrate a version of the invention which has been adapted for use in angio catheter or intra catheter set ups. The discussion that follows is similar to the material above explaining FIGS. 4 and 4a.

The device seen in FIG. 16a has two, cap-elastic, sheath assemblies piggybacked one behind the other. In the first assembly a modified cap 308 has been filled with a putty or gel-like material better seen in FIG. 17. An adhesive backed material 326 is attached to one or more sides of the cap 308. This adhesive is used as necessary to secure cap 308 to the patient's arm. A Teflon® catheter sheath 300 passes through a suitably sized, axially disposed opening in cap 308. In angio catheter or intra catheter applications, the Teflon® catheter sheath 300 is configured to permit axially disposed needle 302 to pass therethrough. The Teflon® catheter sheath is fabricated to include a catheter sheath hub 306 attached to it at one end. Attached to the catheter sheath hub on one or more sides is an adhesive backed material, also 326, that is used to attach the catheter sheath hub to the patient's arm. An elastic sheath means 304 is seen in its contracted state and is attached to the modified cap 308 and catheter sheath hub 306.

In the ready mode, the rear portion of the catheter sheath hub is pushed back against the front face portion of a second modified cap 308a forming a part of a second cap-elastic sheath assembly. In the second cap-sheath assembly, that being the cap sheath assembly to the right of the first one previously described (as seen in FIG. 16a), modified needle cap 308a is seen touching the back of catheter sheath hub 306 when elastic sheath means 304 is in a contracted state. Elastic sheath means 304a is attached to modified needle cap 308a and needle hub 310. The needle 302, connected to hub 310, is axially aligned with and passes through an opening in the face portion of cap 308a, the catheter hub 306, catheter sheath 300 and the opening in safety cap 308. Thus two, modified cap-sheath assemblies are piggybacked one behind the other.

In this version of the invention a safety needle enclosure assembly 314 cooperates with a modified safety needle cap 308. The modified safety needle cap 308 includes arms 316 attached to and projecting outward from the side wall 318 of the modified cap. The attached arms 316 project through slots similar to those identified as 42 in FIG. 4a, in the safety needle enclosure assembly 314. The axial length of the enclosure assembly 314 and the length of the slots are such that when the assembly 314 is in place on the catheter-needle combination and one end of an elastomeric sheath means 304a is secured to the needle hub 310, the arms 316 cooperate with the closed end of the slots to maintain elastomeric sheath means, 304 and 304a, in a contracted, ready condition.

The safety needle enclosure assembly 314 has a smaller diameter, tubular extension 320 sealed at one end, forming a safety cover for the exposed needle tip 322 and Teflon® catheter sheath 300. The smaller diameter tubular extension 320 is confluent with a larger diameter tubular extension 315. The open end of the tubular extension, 315, contacts a needle hub flange 324 when the assembly —cap—sheaths combination 314-308-304-308a-304a are in place and aligned. The needle hub flange, typically, is integrally molded to the hub 310. The enclosure 314 including its length and the relative diameter of tubular extension 320 can be designed so that the outside surface of the face portion of cap 308 corresponding to surface 31 (see FIG. 1). contacts the interior surface of the vertical section as seen in FIG. 4, disposed between the tubular extensions 315 and 320, before arms 316 ever reach the closed ends of the slots. This design, alternatively, can maintain the safety needle cap-catheter assemblies in a ready condition. The whole assembly typically is totally enclosed in a sterilizable foil or plastic wrapper 334 thus maintaining sterility.

As seen in FIG. 16b the foil and the plastic enclosure assembly 314 have been removed. The operator at this point would grasp the handles 316 with his fingers (these handles can have extensions placed if needed or configured as described in one of my copending applications) and needle extension 328 in one hand and remove the assembly 314 with the other hand. The operator would hold needle handles 316 with fingers of one hand and the needle extension 328 would rest in the palm of the same hand. For convenience, two hands could be used. The safety catheter-needle assembly is now ready.

As seen in FIG. 16c, the operator after locating a vein 330 in the patient, guides the needle 302 and Teflon® catheter sheath 300 into the vein with one hand. As the Teflon® catheter sheath assembly with needle is advanced forward into vein 330, the operator grasps needle extension 328 with the other hand and holding handles 316 with the first hand, and the modified cap 308 resting on the patient's arm supplying a firm seat, urges the needle extension 328 until the sheath 300 is in place in the vein. This contracts elastic sheath means 304 and 304a.

Figure 16E:
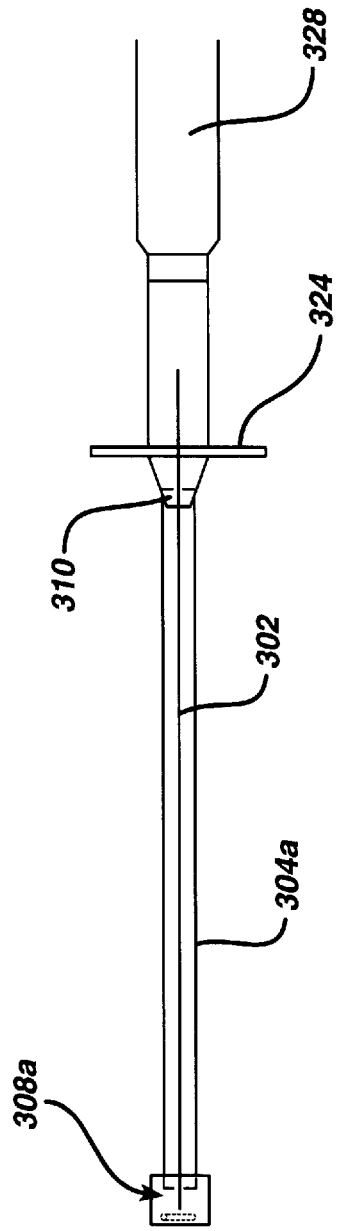
FIGS. 16 a, b, c, d, e and f depict in elevational, side views a further adaptation of the present invention for use with angio-catheters and intra-catheters.
Figure 16F:
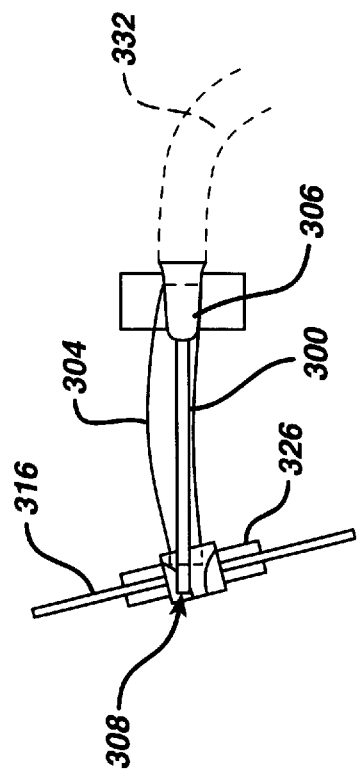

Once the needle and catheter are in place, the adhesive backed material 326 plus additional tape if required, are used to secure the modified cap 308 and Teflon® catheter hub 306 to the patient's arm. This holds elastic sheath means 304 in a contracted state. As seen in FIG. 16d and 16e the needle extension 328 is then pulled back, out from the Teflon catheter sheath 300. The Teflon® sheath remains in the patient's arm. Now I.V. tubing 332 can be attached to Teflon® catheter hub 306.

In 16e the needle has been removed. Elastic sheath means 304a expands back, sliding modified cap 308a forward over needle tip enclosing it within as described above. The various techniques for precluding the needle from reemerging through the cap hole can be employed as well in this adaptation. The hinged flap configuration (FIG. 10) is shown. Needle clogging material and needle embedding material can be employed within the cap 308a, as well.

When the catheter withdraws from the patient's vein, intentionally or by accident, the modified safety cap 308, responsive to the expanding elastic sheath means 304, slides over the end of the catheter that was in place in the patient. The cap-sheath means 304 can be configured and connected in various ways as explained herein to force the Teflon® sheath 300 off axis when its tip enters the enclosed area of the cap. For example, the elastic sheath means 304 can be supplied in a pre-formed arc (see FIG. 13) which would then force cap 308 into this off- axis position.

The Teflon® catheter opening would then become lodged in catheter, clogging material disposed within the cap in a manner similar to that described above for the needle only assembly. Once the opening of the Teflon® catheter is clogged, the flow of the fluid medicine to the patient is slowed and stopped. If the withdrawal of the Teflon® catheter were accidental, and if the patient were unattended, the stopping of the flow of fluid accomplished by the present invention would trigger an alarm alerting medical personnel.

Figure 17:
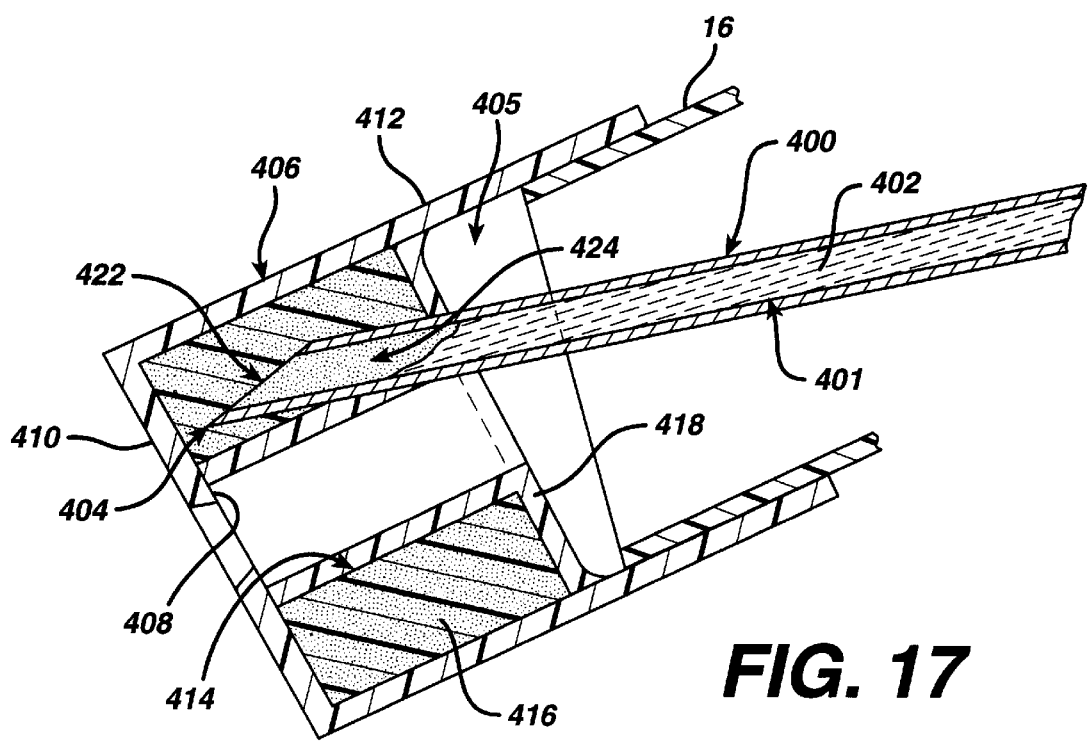
FIG. 17 is an elevational, partial sectional view showing the clogging feature of the present invention applied to angio-catheters.

FIG. 17 depicts the particulars of the Teflon® catheter sheath clogging provisions of the present invention. In this figure, the Teflon® catheter sheath 400 is shown after the assembly has reached the released condition. The Teflon® catheter sheath cavity 401 is seen to still retain the fluid 402 which may be an intravenous solution or body fluid. The Teflon® catheter tip 404 has entered the volume 405 within the safety cap 406 defined by the inside surface 408 of the front face portion 410 and the sidewall 412.

Disposed in this volume in, for example, annular ring form 414 is a Teflon® catheter—clogging material 416 of putty, or gel-like consistency, but viscous enough so as to be able to retain its shape. A suitable material, familiar to dentists, but one of many is CAVIT G, manufactured by EPSE company of Germany, and marketed in the U.S. through Henry Schein Incorporated, of Port Washington, N.Y. Initially of putty-like consistency, when it is contacted by fluid it hardens. The outer diameter of the ring conforms to the inner diameter of the safety cap and, generally, obviates the need to secure the ring to the inner surface of the cap sidewall.

A vapor barrier 418 can be placed over the annular ring 416 to reduce the exposure of the putty-like material to the air so as to keep it from drying out. The barrier also precludes contamination of the catheter by the putty-like material before use. Cellophane or foil is suitable material, but any material that enables the Teflon® catheter tip to penetrate it will do.

Upon reaching the released condition, the Teflon® catheter tip 404, upon entering the volume 405 penetrates the barrier 418 and the ring of Teflon® catheter-clogging material 416. A portion of this material enters the channel 401 containing the fluid and seals off the end 422, eliminating any flow of fluid 402 out of the catheter.

I further envision the application of the principles of the present invention to be used to seal off the end of the intravenous tube that supplies the Teflon® catheter or needle catheter assembly, when there is an accidental interruption of its connection thereto. In this scenario, the intravenous tubing would pass through an axially aligned opening in its respective safety cap before positioning on the catheter hub 306. Elastic sheath means would be secured to a hub-like piece positioned and secured back along the intravenous tubing at one end; and to the tubing safety cap at the other.

At the point the tubing is connected and delivering fluids, the elastomeric sheath means is in a contracted state. If there is an accidental disengagement in the interface between the tubing and its safety cap, the safety cap would be thrust forward along the tubing by the energy stored in the compressed elastic sheath means. The interface end is thus captured within the cap. The cap would include the clogging material discussed above which would fill the tip end of the tubing to effect a seal. Of course, an appropriate alarm mechanism would be triggered, which would bring the disengaged condition to the attention of the necessary personnel.

While the present invention has been disclosed in connection with versions shown and described in detail, various modifications and improvements will become readily apparent to those skilled in the art. Accordingly, the spirit and scope of the present invention is to be limited only by the following claims.

What is claimed is:

1. A safety assembly for use in angiocatheter and intracatheter medical procedures including a first safety cap assembly including a catheter sheath member having a catheter hub portion, said catheter hub portion including means for connecting to a fluid source to be delivered to the circulatory system of a patient, said first safety cap assembly for use in combination with a second safety cap assembly including a needle and needle hub portion for holding the needle, said second safety cap assembly including a second safety cap and a second elastic sheath means, said second elastic sheath means including a first end, said first end connected to said second safety cap said second elastic sheath means including a second end for connecting to the needle hub portion, said second safety cap having at least a front face portion, and side wall means connected to said front face portion and extending back from said front face portion a minimum distance to a rear end, said front face portion of said second safety cap having at least a first opening, larger in diameter than the diameter of the needle, said second safety cap being constructed so as to prevent the passage therethrough of the needle other than through said first opening, said first safety cap assembly comprising:
(a) a first safety cap;
(b) a first elastic sheath means;

said first elastic sheath means including a first end, said first end connected to said first safety cap;

said first elastic sheath means including a second end for connecting to said catheter hub portion;

said first safety cap having at least a respective front face portion and side wall means connected to said front face portion and extending back from said front face portion a minimum distance to a rear end;

said front face portion of said first safety cap having at least a first opening, larger in diameter than an outer diameter of the catheter sheath member;

said catheter sheath member, including said catheter hub portion, having an axially disposed opening of sufficient diameter to permit the needle to pass therethrough, said first safety cap assembly adapted to be axially piggybacked to said second safety cap assembly, wherein the front face portion of said second safety cap assembly is disposed adjacent a first end of said catheter sheath member including said catheter hub portion, such that said first opening of said front face portion of said second safety cap is axially aligned with the axially disposed opening in said catheter sheath means and catheter hub portion and wherein a second end of said catheter sheath member including said catheter hub portion extends through said first opening in the face portion of said first safety cap, in a ready condition;

(c) an enclosure assembly, said enclosure assembly disposed to enclose said first safety cap assembly in its axially piggybacked adaptation with said second safety cap assembly, said enclosure assembly;

(d) means for maintaining said piggybacked adaptation in a ready condition, wherein said first and second elastic sheath means are maintained in a compressed state;

whereupon when an operator is ready to initiate an angiocatheter or intracatheter medical procedure, the operator removes said enclosure assembly, and, while retaining said first safety cap in its axial position on the needle corresponding to its approximate axial position in the ready condition, inserts the needle into the patient's circulatory system and thereafter said second end of said catheter sheath member into the patient's circulatory system;

(e) means for securing said first safety cap and said catheter sheath member including said catheter hub portion at first, respective fixed distances to the point of entry into the patient's circulatory system, said first elastic sheath means maintained in said compressed state when said first safety cap and catheter sheath member are at said first, respective fixed distances, whereupon after securing said first safety cap and said catheter sheath member including said catheter hub portion, at said first, respective fixed distances, said needle is removed from the patient's circulatory system, said second elastic sheath means urging said second safety cap axially along the needle until a tip of the needle is disposed within the volume defined by the side wall means, and front face portion of said second safety cap; and (f) clogging material disposed in said first safety cap, adapted and configured to plug said second end of said catheter sheath member, if said means for securing at said first, respective fixed distances are released so as to cause said second end to disengage from the patient's circulatory system and thereupon said first safety cap to be urged by said first elastic sheath means axially along said catheter sheath member until said second end of said catheter sheath member becomes disposed within said first safety cap in the released condition.

2. The safety assembly claimed in claim 1 wherein needle clogging material is disposed in said second safety cap in a predetermined manner whereby the tip of the needle in the released condition, penetrates the needle-clogging material such that a fluid within the needle is retained therein.

3. The safety assembly claimed in claim 1 wherein a vapor barrier is disposed over the clogging material for said catheter sheath member including said catheter hub portion.

4. The safety assembly claimed in claim 2 wherein a vapor barrier is disposed over the needle clogging material in said second safety cap.

5. The safety assembly claimed in claim 2 further comprising needle tip capturing-material disposed in said second safety cap in a predetermined manner whereby the tip of the needle in the released condition is captured in said needle—tip capturing material.

6. The safety assembly claimed in claim 5 whereby said needle tip—capturing material is disposed between said side wall and said needle clogging material.

7. The safety assembly claimed in claim 6 wherein a vapor barrier is disposed over the needle clogging material.

8. The safety assembly claimed in claim 2 wherein a vapor barrier is disposed over the needle clogging material in said first and second safety caps.

9. The safety assembly claimed in claim 1 wherein said means for connecting to a fluid source to be delivered to the circulatory system of a patient including an intravenous tube having a first end connected to said catheter hub portion and a second end connected to the fluid source, said means for connecting to a fluid source further comprising:

a third safety cap assembly,
said third safety cap assembly comprising,
(a) a third safety cap;
(b) a third elastic sheath means;

said third elastic sheath means including a first end, said first end connected to said third safety cap;

said third elastic sheath means including a second end means for fixedly connecting to the intravenous tube a fixed distance from said first end of the intravenous tube;

said third safety cap having at least a respective front face portion and side wall means connected to said front face portion and extending back from said front face portion a minimum distance to a rear end;

said front face portion of said third safety cap having at least a first opening, larger in diameter than an outer diameter of the intravenous tube, said tube free to move axially in said first opening of said third safety cap;

(e) means for securing said third safety cap and said second end means for fixedly connecting to the intravenous tube a fixed distance from said first end of the intravenous tube, at respective first, fixed distances to the point of connection of said first end of the intravenous tube to said catheter hub portion, said third elastic sheath means maintained in a compressed state when said third safety cap and said second end means are at said respective first, fixed distances, whereupon after securing said third safety cap and said second end means at said respective first, fixed distances, if said first end of the intravenous tube disconnects from said catheter hub portion, said third elastic sheath means will urge said third safety cap axially along the intravenous tube until the first end of the intravenous tube is disposed within the volume defined by the side wall means and front face portion of said third safety cap; and (f) clogging material disposed in said third safety cap, adapted and configured to plug said first end of the intravenous tube when the first end of the intravenous tube becomes disposed within said third safety cap in the released condition.

* * * * *